United States Patent [19]

Ketelsen

[11] 4,056,966

[45] Nov. 8, 1977

[54] APPARATUS FOR CALIBRATION OF A MOISTURE ANALYZER

[76] Inventor: Peter H. Ketelsen, 2162 Georges Lane, Warrington, Pa. 18976

[21] Appl. No.: 760,968

[22] Filed: Jan. 21, 1977

[51] Int. Cl.² .................................................. G01N 31/00
[52] U.S. Cl. .................................................. 73/1 G
[58] Field of Search ......................................... 73/1 G

[56] References Cited

U.S. PATENT DOCUMENTS 3,894,419  7/1975  Mator et al. ........................ 73/1 G

*Primary Examiner*—S. Clement Swisher

[57] ABSTRACT

The apparatus, with a disposable cartridge, is connected into the sample-input-line of the to be calibrated moisture analyzer. The cartridge contains a substance with previously determined, chemically bonded, moisture content.

A motor-driven carriage with a heated section moves slowly along the cartridge, thereby heating a small portion of the cartridge up to a temperature causing the bonded moisture of the substance to release or liberate itself from the substance.

The moisture is then carried with the gas sample into the to be calibrated analyzer and the moisture content in the cartridge may be compared with the moisture determination obtained by the analyzer.

Moisture released from the substance at room temperature has been found negligible.

1 Claim, 3 Drawing Figures

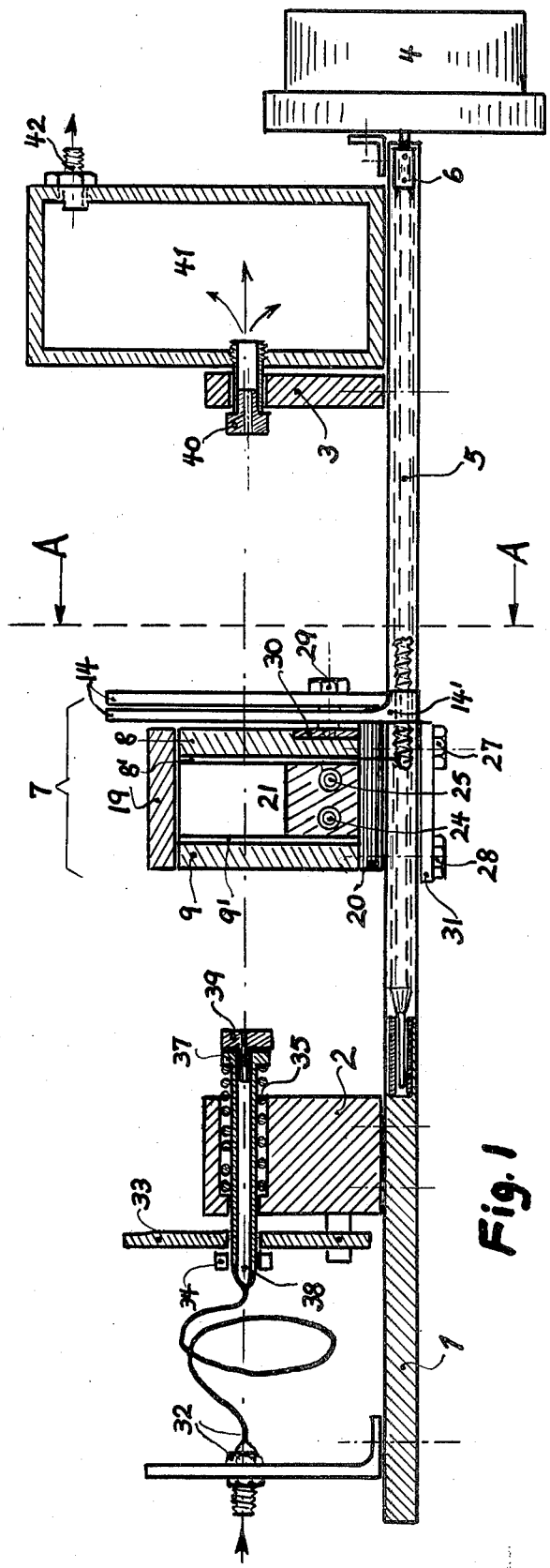

APPARATUS FOR CALIBRATION OF A MOISTURE ANALYZER

This invention relates to an apparatus to calibrate a Measuring Equipment and particularly an instrument for moisture determination in gases.

In practice one may wish to recheck a moisture analyzer in use for proper readouts. A common method is to use bottled gases with known moisture concentration. To obtain these certified bottled gases for calibration usually requires much time and they are inconvenient to install and to handle. Besides, there may be moisture adsorbtion on the inner wall of the bottle and may therefore decrease the concentration of moisture in the certified gases to be measured.

The present invention presents a simple and economic means for calibrating an equipment for moisture determination. It can be operated by a semiskilled person.

The FIG. 1 of the drawing is a cross sectional view of an embodiment of the invention.

FIG. 2 is a side view.

FIG. 3 shows the construction of the cartridge.

Referring to FIG. 1 on the drawing, where 1 is the base plate with a ⅜ inch wide slit 16 (shown in FIG. 2) and mounted on it the posts for the inlet side 2 and on the outlet side 3.

At the end of the base plate 1, a 6 RPM gear reduced synchron motor 4 is mounted and drives the 32 thread per inch threaded rod 5 by means of the coupling 6. The carriage 7, guided in slit 16 and moved by means of the threaded rod 5 and the threaded clamp 14, with spring 15, provides the condition for continuous releasing of the moisture from the cartridge 17. The side walls 8, 9, 10 and 11 are of insulating materials such as: linen based Bakelite and plate 20 is of asbestos. The plate 20, lid 19 and the side walls 8, 9, 10 and 11, with the fissures 8', 9', and 10' and the thin asbestos plate 11', are the enclosures of the aluminum block 21. The block 21 is fastened to the side wall 11 with the screws 22 and 23. Two holes 24 and 25 are insulated with porcelain rings and a proper resistance wire is chosen for heating the block 21. A 5 Volt AC input provides the energy for heating the block to the desired temperature. For example, using Potassium Tartrate the block temperature is about 330° F. (165° C).

To move the carriage manually, the clamp 14, with half thread on each of the clamp arms, opens by pressing the clamp handles 14. The screws 27, 27', 28 and 28' are adjusted for free movement of the carriage in the slit 16 of the base plate 1. The clamp center screw 29 is fastened to a plate 30 inserted in the side wall 8 and the bottom plate 31 holds the carriage in proper place.

The gas-inlet tube 32 is coiled to allow an easy sidewards motion for inserting cartridge 17. Lever 33, with stop-rings 34, spring 35 and stop ring 37 soldered onto the enlarged inlet tubing 38, provide the required spring-action to insert and remove the cartridge 17.

A seal 39 on the inlet or upstream side and 40 on the outlet or downstream side, preferably a material with low wettability, such as Teflon, insures a leakfree insertion of the cartridge 17. Downstream of the cartridge a chamber 41, about 100 ccm volume, and preferably very low wettable material, is connected to equalize differances in minute amounts of moisture liberated from the substance.

The outlet 42 is directly connected to the sample inlet of the to be calibrated moisture analyzer.

Referring to FIG. 2, the clamp 14 with the half thread on each arm 14' and the location in referrance to the base plate 1 and carriage 7 are shown. The location of the cartridge 17 in the notch 43 of the carriage 7 and the hinged lid 19 are shown.

Referring to FIG. 3, the cartridge envelope 17 is a stainless steel tubing of ⅛ inch o.d. About ⅛ inch from each end of the tube a ring 44 and 45 is braced onto it and when inserted they press against the seats 39 and 40.

A Nichrome wire 18, about 0.005 inch o.d. is wetted with epoxy resin, such as Ciba-Geigy Co. Araldite 6010, and coated 36 with a substance which contains chemically bonded moisture, such as Potassium Tartrate or others and then inserted into the cartridge envelope.

The physical size of the substance coated on the wire 18 determins the readout. For example, using Potassium Tartrate, crystal size between mesh 100 and mesh 120, the average readout on the analyzer was 290 ppm/vol. Using crystal sizes smaller than 120 mesh, the average reading was 135 ppm/vol. However, the total amount of moisture measured by the analyzer was on both crystal sizes within 4% of the previous determined moisture content.

The weight of the substance is determined with an analytical balance and the moisture content calculated.

It is understood that the given construction of the cartridge, mentioned above, is a sample. The material of the cartridge-envelope can be of pyrex glass or other materials, heatable to well above the to be used temperature and possibly very low moisture adsorbtion. Several substances with chemically bonded $H_2O$ can be used, but for moisture stability, hydroscopic substances should not be used.

For field use, this apparatus may be equipped with DC motor and proper heating element for battery operation.

What is claimed is:

1. A device for introducing a gaseous mixture of known moisture content into an analyzer for calibration purposes comprising a cartridge consisting of a tubular member and a wire longitudinally mounted within the tubular member, the wire being coated with a substance having chemically bonded moisture which is released when the substance is heated, means for connecting the cartridge to a source of gas at one end and to an analyzer at the other end, means mounting the cartridge and a carriage for movement along the length of the cartridge, heater means mounted on the carriage for heating a portion of the cartridge along its length and means for advancing the carriage along the length of the cartridge at a uniform speed.

* * * * *